US00PP32647P3

(12) United States Plant Patent
Hofmann

(10) Patent No.: US PP32,647 P3
(45) Date of Patent: Dec. 15, 2020

(54) ***BIDENS* PLANT NAMED 'INBIDCAMEM'**

(50) Latin Name: *Bidens ferulifolia*
Varietal Denomination: INBIDCAMEM

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 16/873,425

(22) Filed: Apr. 11, 2020

(65) Prior Publication Data

US 2020/0329606 P1 Oct. 15, 2020

(30) Foreign Application Priority Data

Apr. 15, 2019 (CA) ..... PBR 19-9758

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Bidens* plant named 'INBIDCAMEM', characterized by its compact, upright to outwardly spreading and uniformly mounding plant habit; moderately vigorous to vigorous growth habit; freely branching habit; dense and bushy plant form; freely flowering habit; long flowering period; and single-type inflorescences with orange red and bright yellow bi-colored ray florets.

1 Drawing Sheet

Botanical designation: *Bidens ferulifolia.*

Cultivar denomination: 'INBIDCAMEM'.

Cross-Reference to a Related Application and Statement Regarding Prior Disclosures by Inventor/Applicant:

This application claims priority to a Canadian Plant Breeders' Rights application filed on Apr. 15, 2019, application number 19-9758. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Bidens* plant, botanically known as *Bidens ferulifolia* and hereinafter referred to by the name 'INBIDCAMEM'.

The new *Bidens* plant is a product of a planned breeding program conducted by the Inventor in Heidesheim, Germany. The objective of the breeding program is to create new uniformly mounding *Bidens* plants with unique ray floret coloration.

The new *Bidens* plant originated from a cross-pollination made by the Inventor in Heidesheim, Germany in July, 2014 of a proprietary selection of *Bidens ferulifolia* identified as code number B13-4035-1, not patented, as the female, or seed, parent with a proprietary selection of *Bidens ferulifolia* identified as code number B13-4018-1, not patented, as the male, or pollen, parent. The new *Bidens* plant was discovered and selected by the Inventor as a single flowering plant from within the progeny of the stated cross-pollination in a controlled greenhouse environment in Heidesheim, Germany in March, 2017.

Asexual reproduction of the new *Bidens* plant by vegetative terminal cuttings in a controlled environment in Gensingen, Germany since May, 2017 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'INBIDCAMEM'. These characteristics in combination distinguish 'INBIDCAMEM' as a new and distinct *Bidens* plant:

1. Compact, upright to outwardly spreading and uniformly mounding plant habit.
2. Moderately vigorous to vigorous growth habit.

3. Freely branching habit; dense and bushy plant form.
4. Freely flowering habit.
5. Long flowering period.
6. Single-type inflorescences with orange red and bright yellow bi-colored ray florets.

Plants of the new *Bidens* differ primarily from plants of the female parent selection in the following characteristics:

1. Plants of the new *Bidens* are more compact and denser than plants of the female parent selection.
2. Plants of the new *Bidens* have smaller inflorescences than plants of the female parent selection.
3. Ray florets of plants of the new *Bidens* are orange red and bright yellow in color whereas ray florets of plants of the female parent selection are red in color with yellow apices.

Plants of the new *Bidens* differ primarily from plants of the male parent selection in the following characteristics:

1. Plants of the new *Bidens* are more compact and denser than plants of the male parent selection.
2. Plants of the new *Bidens* have smaller inflorescences than plants of the male parent selection.
3. Ray florets of plants of the new *Bidens* are orange red and bright yellow in color whereas ray florets of plants of the male parent selection are yellow in color.

Plants of the new *Bidens* can be compared to plants of *Bidens ferulifolia* 'KOIBID1510', disclosed in U.S. Plant Pat. No. 29,694. In side-by-side comparisons, plants of the new *Bidens* differ primarily from plants of 'KOIBID1510' in the following characteristics:

1. Plants of the new *Bidens* are more compact than plants of 'KOIBID1510'.
2. Plants of the new *Bidens* have larger inflorescences than plants of 'KOIBID1510'.

Plants of the new *Bidens* can also be compared to plants of *Bidens ferulifolia* 'Beedance Painted Red', not patented. In side-by-side comparisons, plants of the new *Bidens* differ primarily from plants of 'Beedance Painted Red' in the following characteristics:

1. Plants of the new *Bidens* are more compact than plants of 'Beedance Painted Red'.
2. Plants of the new *Bidens* have larger inflorescences than plants of 'Beedance Painted Red'.

BRIEF DESCRIPTION OF THE PHOTOGRAPHS

The accompanying colored photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

At the top of the photographic sheet (FIG. 1) is a side perspective view of a typical flowering plant of 'INBIDCAMEM' grown in a container and at the bottom of the photographic sheet is a close-up view of a typical flowering plant of 'INBIDCAMEM'.

DETAILED BOTANICAL DESCRIPTION

The aforementioned photographs and following observations and measurements describe plants grown during the summer in 15.25-cm containers in a polyethylene-covered greenhouse in St. Thomas, Ontario, Canada and under cultural practices typical of commercial *Bidens* production. During the production of the plants, day temperatures averaged 30° C. and night temperatures averaged 15° C. Plants were pinched when rooted cuttings were planted and were nine weeks from planting rooted cuttings when the photographs and description were taken. In the following description, color references are made to The Royal Horticultural Society Colour Chart, 2007 Edition, except where general terms of ordinary dictionary significance are used.

Botanical classification: *Bidens ferulifolia* 'INBIDCAMEM'.

Parentage:

*Female, or seed, parent*.—Proprietary selection of *Bidens ferulifolia* identified as code number B13-4035-1, not patented.

*Male, or pollen, parent*.—Proprietary selection of *Bidens ferulifolia* identified as code number B13-4018-1, not patented.

Propagation:

*Type*.—By vegetative terminal cuttings.

*Time to initiate roots, summer*.—About one week at temperatures about 23° C.

*Time to initiate roots, winter*.—About two weeks at temperatures about 23° C.

*Time to produce a rooted young plant, summer*.—About three to four weeks at temperatures about 23° C.

*Time to produce a rooted young plant, winter*.—About four to five weeks at temperatures about 10° C. to 15° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Compact, upright to outwardly spreading and uniformly mounding plant habit; moderately vigorous to vigorous growth habit and moderate to rapid growth rate.

*Branching habit*.—Freely branching habit typically with about eight primary lateral branches each with about seven secondary lateral branches each with about four tertiary lateral branches developing per plant; dense and bushy appearance.

*Plant height*.—About 17.8 cm.

*Plant diameter or spread*.—About 40 cm.

*Lateral branches*.—Length, primary branches: About 18.1 cm. Diameter, primary branches: About 3.3 mm. Internode length: About 2.5 cm. Strength: Strong, flexible. Aspect: Upright to outwardly. Texture and luster: Densely pubescent; matte. Color, developing: Close to 147D slightly tinged with close to N77A. Color, developed: Close to 147C moderately to strongly tinged with close to N77A.

Leaf description:

*Arrangement*.—Opposite, simple.

*Length*.—About 3.5 cm.

*Width*.—About 3.4 cm.

*Shape*.—Roughly deltoid, pinnatisect; tri-lobed.

*Apex*.—Acute with mucronate tip.

*Base*.—Cuneate.

*Margin*.—Serrate.

*Texture and luster, upper surface*.—Slightly pubescent; slightly glossy.

*Texture and luster, lower surface*.—Slightly to moderately pubescent; matte.

*Venation pattern*.—Pinnate, reticulate.

*Color*.—Developing leaves, upper surface: Close to 138A. Developing leaves, lower surface: Close to 138B. Fully expanded leaves, upper surface: Close to 137A; venation, close to 144C. Fully expanded leaves, lower surface: Close to 147B; venation, close to 146B.

*Petioles*.—Length: About 8 mm. Diameter: About 1.2 mm. Strength: Moderately strong, flexible. Texture and luster, upper and lower surfaces: Moderately pubescent; matte. Color, upper surface: Close to 145C. Color, lower surface: Close to 146C.

Inflorescence description:

*Appearance*.—Single type (daisy) solitary inflorescences developing on terminal and axillary peduncles; inflorescence form with ray and disc florets; inflorescences positioned on peduncles; inflorescences face mostly upright.

*Flowering habit*.—Freely flowering habit with more than 1,000 inflorescences and inflorescence buds developing during the flowering season.

*Fragrance*.—Moderate, earthy.

*Flowering response*.—Early flowering habit, plants begin flowering about five to seven weeks after planting.

*Natural flowering season*.—Long flowering period, plants flower continuously from spring until frost in temperate regions and year-round in milder (above freezing) climates.

*Inflorescence longevity*.—Inflorescences last about seven days on the plant; inflorescences persistent.

*Inflorescence buds*.—Height: About 3.5 mm. Diameter: About 4 mm. Shape: Rounded. Texture and luster: Densely pubescent; matte. Color: Close to 148A.

*Inflorescence size*.—Diameter: About 3.7 cm. Height: About 8 mm. Disc diameter: About 7.5 mm.

*Receptacles*.—Receptacle diameter: About 5 mm. Receptacle height: About 5 mm. Receptacle shape: Small, cup-shaped. Receptacle color: Close to 137D.

*Ray florets*.—Number of ray florets per inflorescence: About eight arranged in a single whorl. Length: About 1.7 cm. Width: About 8 mm. Shape: Ovate. Apex: Shallowly emarginate. Base: Rounded. Margin: Entire; not undulate. Aspect: Mostly horizontal, apices slightly reflexing with development. Texture and luster, upper and lower surfaces: Longitudinally ribbed, glabrous; matte. Color: When opening, upper surface: Distally, close to 185A and proximally, close to 13A. When opening, lower surface: Distally, close to 180A and proximally, close to 13A. Fully opened, upper surface: Distally, close to 179A and 169B and proximally, close to 14A; venation, similar to lamina; with development, distally, becoming closer to 26A tinged with 42D and proximally, closer to 9A. Fully opened, lower surface: Distally, close to 39B and proximally, close to 12A; venation, close to 1D; with development, distally, becoming closer to 34D and proximally, closer to 9A.

*Disc florets*.—Number of disc florets per inflorescence: About 75 in about five whorls at the center of the receptacle. Length: About 5 mm. Diameter: Less than 1 mm. Shape: Tubular, slender; apex, five-pointed. Texture and luster: Smooth, glabrous; slightly glossy. Color: When opening, inner and outer surfaces: Close to 153D and at the base, close to 1D. Fully opened, inner and outer surfaces: Close to 153D and at the base, close to 1D.

*Phyllaries*.—Quantity per inflorescence: About 28 arranged in about two to three whorls. Length: About 4 mm. Width: About 1 mm. Shape: Linear. Apex: Acute. Base: Truncate. Margin: Entire. Texture and luster, upper and lower surfaces: Slightly pubescent; matte. Color, upper and lower surfaces: Close to 137B.

*Peduncles*.—Length, terminal peduncle: About 2.9 cm. Length, third peduncle: About 4.7 cm. Diameter: Less than 1 mm. Strength: Strong; flexible. Aspect: Terminal peduncles, mostly erect; axillary peduncles, about 45° from vertical. Texture and luster: Densely pubescent; matte. Color: Close to 145B.

*Reproductive organs*.—Androecium: Present on disc florets only. Quantity per disc floret: Five. Filament length: About 2 mm. Filament color: Close to 144D. Anther size: About 1 mm by 2 mm. Anther shape: Ellipsoidal. Anther color: Close to 200A. Pollen amount: Scarce. Pollen color: Close to N25C. Gynoecium: Present on disc and ray florets. Quantity per floret: One. Pistil length: About 5 mm. Style length: About 3.5 mm. Style color: Close to 14B. Stigma diameter: Less than 1 mm. Stigma shape: Bi-parted. Stigma color: Close to 14A. Ovary color: Close to 144D.

*Seeds and fruits*.—To date, seed and fruit development have not been observed on plants of the new *Bidens*.

Pathogen & pest resistance: To date, plants of the new *Bidens* have not been shown to be resistant to pathogens and pests common to *Bidens* plants.

Garden performance: Plants of the new *Bidens* have been observed to have good garden performance and to tolerate temperatures from about 2° C. to about 40° C. and are suitable for USDA Hardiness Zones 9 and 11.

It is claimed:

1. A new and distinct *Bidens* plant named 'INBIDCAMEM' as illustrated and described.

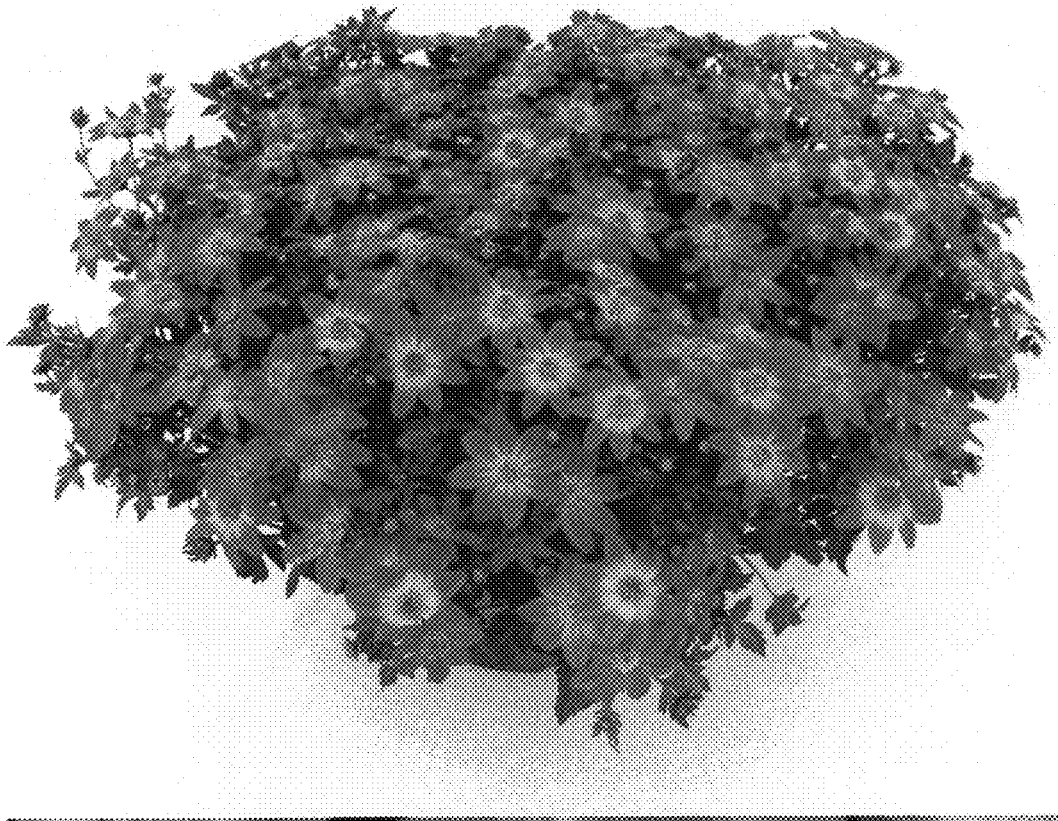
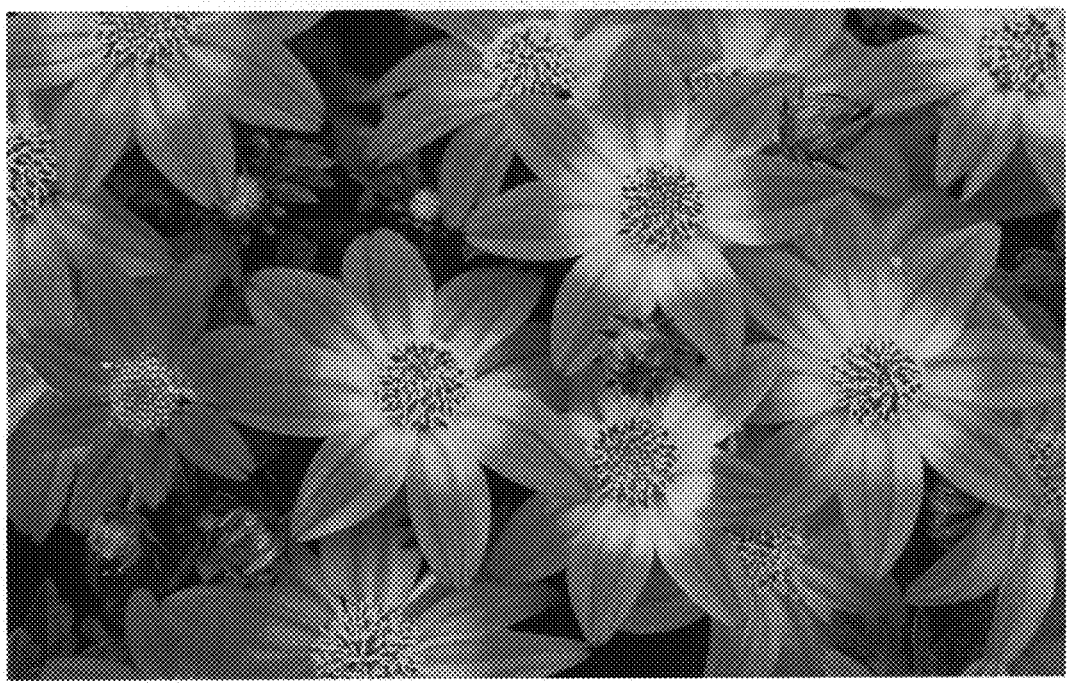

* * * * *